US008394409B2

(12) United States Patent
Odidi et al.

(10) Patent No.: US 8,394,409 B2
(45) Date of Patent: Mar. 12, 2013

(54) CONTROLLED EXTENDED DRUG RELEASE TECHNOLOGY

(75) Inventors: Isa Odidi, Toronto (CA); Amina Odidi, Toronto (CA)

(73) Assignee: Intellipharmaceutics Corp., Ontario (CA)

( * ) Notice: Subject to any disclaimer, the term of this patent is extended or adjusted under 35 U.S.C. 154(b) by 743 days.

(21) Appl. No.: 10/880,474

(22) Filed: Jul. 1, 2004

(65) Prior Publication Data

US 2006/0003007 A1   Jan. 5, 2006

(51) Int. Cl.
A61K 9/24 (2006.01)
(52) U.S. Cl. ........ 424/472; 424/473; 424/451; 424/466; 424/468
(58) Field of Classification Search ........................ None
See application file for complete search history.

(56) References Cited

U.S. PATENT DOCUMENTS

| | | | |
|---|---|---|---|
| 2,540,979 A | 2/1951 | MacDonnell | |
| 3,254,088 A | 5/1966 | Juda et al. | |
| 3,493,657 A | 2/1970 | Lewenstein | |
| 3,629,393 A | 12/1971 | Nakamoto et al. | |
| 3,728,445 A | 4/1973 | Bardani | |
| 3,773,955 A | 11/1973 | Pachter | |
| 3,789,117 A | 1/1974 | Tsujino | |
| 3,819,706 A | 6/1974 | Mehta | |
| 3,845,770 A | 11/1974 | Higuchi | |
| 3,856,721 A | 12/1974 | Fritschel | |
| 3,916,899 A | 11/1975 | Theeuwes et al. | |
| 4,008,719 A | 2/1977 | Theeuwes | |
| 4,016,880 A | 4/1977 | Theeuwes | |
| 4,034,758 A | 7/1977 | Theeuwes | |
| 4,036,228 A | 7/1977 | Theeuwes | |
| 4,045,563 A | 8/1977 | Berntsson et al. | |
| 4,060,598 A | 11/1977 | Groppenbacher et al. | |
| 4,077,407 A | 3/1978 | Theeuwes | |
| 4,160,452 A | 7/1979 | Theeuwes | |
| 4,161,477 A | 7/1979 | Long | |
| 4,183,838 A | 1/1980 | Gagliani | |
| 4,183,839 A | 1/1980 | Gagliani | |
| 4,193,985 A | 3/1980 | Bechgaard | |
| 4,200,098 A | 4/1980 | Ayer | |
| 4,218,433 A | 8/1980 | Kooichi et al. | |
| 4,248,856 A | 2/1981 | Guley et al. | |
| 4,250,136 A | 2/1981 | Rex | |
| 4,252,786 A | 2/1981 | Weiss et al. | |
| 4,255,431 A | 3/1981 | Junggren et al. | |
| 4,309,405 A | 1/1982 | Guley et al. | |
| 4,327,725 A | 5/1982 | Cortese | |
| 4,330,338 A | 5/1982 | Banker | |
| 4,337,257 A | 6/1982 | Junggren | |
| 4,389,393 A | 6/1983 | Schor | |
| 4,425,441 A | 1/1984 | Gagliani et al. | |
| 4,457,933 A | 7/1984 | Gordon | |
| 4,461,759 A | 7/1984 | Dunn | |
| 4,486,412 A | 12/1984 | Shah et al. | |
| 4,508,905 A | 4/1985 | Junggren | |
| 4,514,538 A | 4/1985 | Shvakhman et al. | |
| 4,517,112 A | 5/1985 | Mardis et al. | |
| 4,518,717 A | 5/1985 | Long et al. | |
| 4,545,412 A | 10/1985 | Gamberini | |
| 4,582,835 A | 4/1986 | Lewis | |
| 4,606,909 A | 8/1986 | Bechgaard | |
| 4,610,870 A | 9/1986 | Jain et al. | |
| 4,612,008 A | 9/1986 | Wong et al. | |
| 4,628,098 A | 12/1986 | Nohara et al. | |
| 4,666,705 A | 5/1987 | DeCrosta et al. | |
| 4,676,929 A | 6/1987 | Rittler | |
| 4,684,516 A | 8/1987 | Bhutani | |
| 4,686,230 A | 8/1987 | Rainer et al. | |
| 4,689,333 A | 8/1987 | Nohara et al. | |
| 4,704,285 A | 11/1987 | Alderman | |
| 4,708,834 A | 11/1987 | Cohen et al. | |
| 4,713,248 A * | 12/1987 | Kjornaes et al. | 424/468 |
| 4,756,911 A | 7/1988 | Drost et al. | |
| 4,758,579 A | 7/1988 | Kohl et al. | |
| 4,765,989 A | 8/1988 | Wong et al. | |
| 4,783,337 A | 11/1988 | Wong et al. | |
| 4,786,505 A | 11/1988 | Lovgren et al. | |
| 4,812,446 A | 3/1989 | Brand | |
| 4,818,760 A | 4/1989 | Binder et al. | |
| 4,832,958 A | 5/1989 | Baudier et al. | |
| 4,844,905 A * | 7/1989 | Ichikawa et al. | 424/451 |
| 4,845,118 A | 7/1989 | Lang et al. | |
| 4,851,228 A | 7/1989 | Zentner et al. | |
| 4,853,230 A | 8/1989 | Lovgren et al. | |
| 4,869,908 A | 9/1989 | Kirschner et al. | |
| 4,880,631 A | 11/1989 | Haslam | |
| 4,886,668 A | 12/1989 | Haslam | |
| 4,892,742 A | 1/1990 | Shah | |
| 4,900,557 A | 2/1990 | Dell et al. | |
| 4,904,476 A | 2/1990 | Mehta et al. | |

(Continued)

FOREIGN PATENT DOCUMENTS

CA   2286684 A1   10/1998
CA   2529984 A1   12/2004

(Continued)

OTHER PUBLICATIONS

Deshpande et al., Development of a Novel Controlled-Release System for Gastric Retention, Pharmaceutical Research, vol. 14 No. 6 1997 pp. 815-819.*

(Continued)

Primary Examiner — Dennis Heyer
(74) Attorney, Agent, or Firm — Thomas Horstemeyer, LLP

(57) ABSTRACT

A controlled extended drug release technology for the controlled extended release of hydrophobic or hydrophilic drugs or therapeutically active agents consisting of a homogeneous blend of one or more therapeutic agents, gas generators and surrounded by one or more layers of coat made of thermoplastic water insoluble cellulose derivatives, acrylic polymers, superdisintegrants and optionally an oil, antioxidants and electrolytes. The technology platform is capable of releasing therapeutic agents via zero, first or pseudo first order release.

19 Claims, No Drawings

U.S. PATENT DOCUMENTS

| | | | |
|---|---|---|---|
| 4,927,640 A | 5/1990 | Dahlinder et al. |
| 4,935,243 A | 6/1990 | Borkan et al. |
| 4,940,587 A | 7/1990 | Jenkins et al. |
| 4,940,588 A | 7/1990 | Sparks et al. |
| 4,946,853 A | 8/1990 | Bannon et al. |
| 4,963,365 A | 10/1990 | Samejima et al. |
| 4,965,269 A | 10/1990 | Brandstrom et al. |
| 4,966,768 A | 10/1990 | Michelucci et al. |
| 5,000,962 A | 3/1991 | Sangekar et al. |
| 5,004,614 A | 4/1991 | Staniforth |
| 5,021,433 A | 6/1991 | Alminger et al. |
| 5,028,434 A | 7/1991 | Barclay et al. |
| 5,045,552 A | 9/1991 | Souda et al. |
| 5,049,394 A | 9/1991 | Howard |
| 5,071,643 A | 12/1991 | Yu et al. |
| 5,073,384 A | 12/1991 | Valentine et al. |
| 5,077,051 A | 12/1991 | Gallopo |
| 5,123,146 A | 6/1992 | Olson |
| 5,149,702 A | 9/1992 | Yamada et al. |
| 5,190,763 A | 3/1993 | Edgren et al. |
| 5,202,128 A | 4/1993 | Morella et al. |
| 5,219,572 A | 6/1993 | Sivaramakrishnan |
| 5,229,131 A | 7/1993 | Amidon et al. |
| 5,236,714 A | 8/1993 | Lee et al. |
| 5,240,712 A | 8/1993 | Smith |
| 5,252,339 A | 10/1993 | Cristofori et al. |
| 5,260,069 A | 11/1993 | Chen |
| 5,286,497 A | 2/1994 | Hendrickson et al. |
| 5,288,500 A | 2/1994 | Ibsen |
| 5,290,816 A | 3/1994 | Blumberg |
| 5,330,766 A | 7/1994 | Morella et al. |
| 5,376,388 A | 12/1994 | Meyers |
| 5,378,474 A | 1/1995 | Morella et al. |
| 5,393,528 A | 2/1995 | Staab |
| 5,415,871 A | 5/1995 | Pankhania et al. |
| 5,430,042 A | 7/1995 | Lindberg et al. |
| 5,445,829 A | 8/1995 | Paradissis et al. |
| 5,458,887 A | 10/1995 | Chen et al. |
| 5,472,711 A | 12/1995 | Baichwal |
| 5,480,335 A | 1/1996 | Caveza |
| 5,503,846 A | 4/1996 | Wehling |
| 5,508,040 A | 4/1996 | Chen |
| 5,595,762 A | 1/1997 | Derrieu |
| 5,681,581 A | 10/1997 | Dunn |
| 5,708,017 A | 1/1998 | Dave et al. |
| 5,713,000 A | 1/1998 | Larson |
| 5,736,159 A | 4/1998 | Chen et al. |
| 5,753,265 A | 5/1998 | Bergstrand |
| 5,759,577 A | 6/1998 | Barcomb |
| 5,780,055 A | 7/1998 | Habib et al. |
| 5,783,215 A | 7/1998 | Arwidsson et al. |
| 5,795,583 A | 8/1998 | Grune et al. |
| 5,800,422 A | 9/1998 | Dong et al. |
| 5,817,338 A | 10/1998 | Bergstrand |
| 5,840,329 A | 11/1998 | Bai |
| 5,840,910 A | 11/1998 | Souda |
| 5,879,708 A | 3/1999 | Makino et al. |
| 5,955,106 A | 9/1999 | Moeckel |
| 5,972,329 A | 10/1999 | Chuang et al. |
| 5,998,445 A | 12/1999 | Souda et al. |
| 6,022,562 A | 2/2000 | Autant et al. |
| 6,039,975 A | 3/2000 | Shah et al. |
| 6,046,177 A | 4/2000 | Stella et al. |
| 6,068,853 A | 5/2000 | Giannos et al. |
| 6,090,401 A | 7/2000 | Gowan et al. |
| 6,099,859 A | 8/2000 | Cheng et al. |
| 6,106,864 A | 8/2000 | Dolan et al. |
| 6,183,776 B1 | 2/2001 | Depui et al. |
| 6,183,777 B1 | 2/2001 | Chen et al. |
| 6,210,710 B1 | 4/2001 | Skinner |
| 6,228,400 B1 | 5/2001 | Lee et al. |
| 6,251,432 B1 | 6/2001 | Mazer et al. |
| 6,270,804 B1 | 8/2001 | Getz et al. |
| 6,296,876 B1 | 10/2001 | Odidi et al. |
| 6,312,724 B1 | 11/2001 | Odidi et al. |
| 6,368,635 B1 | 4/2002 | Akiyama et al. |
| 6,433,040 B1 | 8/2002 | Dellamary et al. |
| 6,479,075 B1 * | 11/2002 | Odidi et al. ............... 424/458 |
| 6,489,346 B1 | 12/2002 | Phillips |
| 6,491,949 B2 | 12/2002 | Faour et al. |
| 6,509,037 B2 | 1/2003 | Odidi |
| 6,555,127 B2 | 4/2003 | Steiner |
| 6,558,704 B1 | 5/2003 | Bartholomaeus |
| 6,569,453 B2 | 5/2003 | Linder et al. |
| 6,599,529 B1 | 7/2003 | Skinhoj |
| 6,605,300 B1 | 8/2003 | Burnside et al. |
| 6,607,751 B1 | 8/2003 | Odidi et al. |
| 6,627,635 B2 | 9/2003 | Palermo et al. |
| 6,645,524 B2 | 11/2003 | Midha et al. |
| 6,645,528 B1 | 11/2003 | Straub et al. |
| 6,645,988 B2 | 11/2003 | Phillips |
| 6,652,882 B1 | 11/2003 | Odidi et al. |
| 6,673,367 B1 | 1/2004 | Goldenheim et al. |
| 6,676,966 B1 | 1/2004 | Odidi et al. |
| 6,696,088 B2 | 2/2004 | Oshlack et al. |
| 6,699,885 B2 | 3/2004 | Phillips |
| 6,780,882 B2 | 8/2004 | Phillips |
| 6,800,668 B1 | 10/2004 | Odidi et al. |
| 6,902,742 B2 | 6/2005 | Devane et al. |
| 6,911,217 B1 | 6/2005 | Gren et al. |
| 6,946,146 B2 | 9/2005 | Mulye |
| 7,090,867 B2 | 8/2006 | Odidi et al. |
| 7,135,465 B2 | 11/2006 | Abramowitz et al. |
| 7,157,103 B2 | 1/2007 | Sackler |
| 7,858,119 B1 | 12/2010 | Odidi et al. |
| 7,906,143 B1 | 3/2011 | Odidi et al. |
| 2001/0006649 A1 | 7/2001 | Chen |
| 2002/0002147 A1 | 1/2002 | Abramowitz et al. |
| 2002/0045646 A1 | 4/2002 | Phillips |
| 2002/0086885 A1 | 7/2002 | Odaka et al. |
| 2002/0110590 A1 | 8/2002 | Shaked et al. |
| 2002/0128293 A1 | 9/2002 | Rampal et al. |
| 2002/0132005 A1 * | 9/2002 | Faour ............................ 424/473 |
| 2002/0150535 A1 | 10/2002 | Madras et al. |
| 2003/0064099 A1 | 4/2003 | Oshlack et al. |
| 2003/0064101 A1 * | 4/2003 | Mehta et al. .................. 424/473 |
| 2003/0068071 A1 | 4/2003 | Oshlack et al. |
| 2003/0118641 A1 | 6/2003 | Maloney et al. |
| 2003/0118669 A1 | 6/2003 | Phillips |
| 2003/0185887 A1 | 10/2003 | Chen et al. |
| 2003/0215507 A1 | 11/2003 | Sherman et al. |
| 2003/0215527 A1 | 11/2003 | Phillips |
| 2003/0220413 A1 | 11/2003 | Petereit et al. |
| 2003/0228361 A1 * | 12/2003 | Baichwal et al. ............. 424/468 |
| 2003/0235616 A1 | 12/2003 | Sowden et al. |
| 2004/0048896 A1 | 3/2004 | Phillips |
| 2004/0058018 A1 | 3/2004 | Phillips |
| 2004/0101558 A1 | 5/2004 | Dietrich et al. |
| 2004/0131669 A1 | 7/2004 | Kerc |
| 2004/0171646 A1 | 9/2004 | Phillips |
| 2004/0265370 A1 | 12/2004 | Odidi et al. |
| 2004/0265380 A1 * | 12/2004 | Delmas et al. ................ 424/466 |
| 2005/0004171 A1 | 1/2005 | Phillips |
| 2005/0042304 A1 | 2/2005 | Phillips |
| 2005/0054682 A1 | 3/2005 | Phillips |
| 2005/0186268 A1 | 8/2005 | Hoshi et al. |
| 2005/0196436 A1 | 9/2005 | Chantranukul et al. |
| 2006/0003001 A1 | 1/2006 | Devane et al. |
| 2006/0004193 A1 | 1/2006 | Muller |
| 2006/0017336 A1 | 1/2006 | Knauff |
| 2006/0024361 A1 | 2/2006 | Odidi |
| 2006/0039864 A1 | 2/2006 | Bartholomaus et al. |
| 2006/0039976 A1 | 2/2006 | Odidi et al. |
| 2006/0099246 A1 | 5/2006 | Tanner et al. |
| 2006/0153909 A1 | 7/2006 | Motoune |
| 2006/0205681 A1 | 9/2006 | Moaddeb |
| 2007/0003619 A1 | 1/2007 | Smith |
| 2007/0077293 A1 | 4/2007 | Park |
| 2007/0104778 A1 | 5/2007 | Zeng et al. |
| 2007/0131357 A1 | 6/2007 | Wu |
| 2007/0166370 A1 | 7/2007 | Odidi et al. |
| 2009/0220613 A1 | 9/2009 | Odidi et al. |

FOREIGN PATENT DOCUMENTS

| | | |
|---|---|---|
| DE | 3943242 A1 | 6/1990 |
| EP | 0005129 B1 | 4/1981 |
| EP | 0157695 A2 | 9/1985 |

| | | | |
|---|---|---|---|
| EP | 0174726 A1 | 3/1986 |
| EP | 0184322 B1 | 6/1986 |
| EP | 080341 B1 | 10/1987 |
| EP | 0261478 A1 | 3/1988 |
| EP | 0268956 B1 | 6/1988 |
| EP | 0270305 A2 | 6/1988 |
| EP | 0342522 A1 | 11/1989 |
| EP | 0366321 A1 | 5/1990 |
| EP | 0403383 A1 | 12/1990 |
| EP | 0434999 B1 | 7/1991 |
| EP | 0453001 A1 | 10/1991 |
| EP | 0527638 A1 | 2/1993 |
| EP | 0797991 A1 | 10/1997 |
| EP | 0960620 A1 | 12/1999 |
| EP | 1017370 B1 | 7/2000 |
| FR | 2624012 | 9/1989 |
| GB | 2134516 A | 8/1984 |
| GB | 2163747 A | 3/1986 |
| HU | 203477 B | 1/1991 |
| JP | 2002-068964 | 3/2002 |
| JP | 2005508359 | 3/2005 |
| JP | 2005515153 | 5/2006 |
| WO | WO8503436 A1 | 8/1985 |
| WO | WO8705212 A1 | 9/1987 |
| WO | WO9011070 A1 | 10/1990 |
| WO | WO9107950 A1 | 6/1991 |
| WO | WO9116885 A1 | 11/1991 |
| WO | WO9204013 A1 | 3/1992 |
| WO | WO9208716 A1 | 5/1992 |
| WO | WO9323770 A1 | 7/1993 |
| WO | WO9428882 A1 | 12/1994 |
| WO | WO9816206 A1 | 4/1998 |
| WO | WO9851287 A1 | 11/1998 |
| WO | WO9912524 A1 | 3/1999 |
| WO | 0230398 A2 | 4/2002 |
| WO | WO0230398 A2 | 4/2002 |
| WO | WO/02/085336 | * 10/2002 |
| WO | WO03009846 A1 | 2/2003 |
| WO | 03086364 A1 | 10/2003 |
| WO | WO04000825 A1 | 12/2003 |
| WO | WO2004056354 A1 | 7/2004 |
| WO | 2005021009 A2 | 3/2005 |
| WO | 2005032474 | 4/2005 |
| WO | 2005065661 A2 | 7/2005 |
| WO | 2005097075 | 10/2005 |
| WO | 2006011592 | 2/2006 |
| WO | 2006017336 A2 | 2/2006 |
| WO | 2006085335 A2 | 8/2006 |

OTHER PUBLICATIONS

Conner et al. A scintigraphic study to investigrate the potential for altered gut distribution of loperaminde from a loperaminde-simethicone formulation in man, European Journal of Pharmaceutical Sciences, 13 (2001) p. 369-374.*
Sungthongjeen et al. Development of pulsatile release tablets with swelling and rupturable layers, Journal of Controlled Release, 95 (2004) p. 147-159.*
Krögel et al., Floating or pulsatile drug delivery systems based on coated efferescent cores, 1999, International J. Pharma, 187, 175-184.*
Krögel et al. in International Journal of Pharmaceutics 187 (1999) 175-184.*
Anderson, M. et al., Analysis of Film Coating Thickness and Surface Area of Pharmaceutical Pellets using Fluorescence Microscopy and Image Analysis, J. Pharmaceutical and Biomedical Analysis, (2000), vol. 22, pp. 325-339.
Arora, S. et al, Pulsatie Drug Delivery Systems: An Approach for Controlled Drug Delivery, Indian J. Pharm. Sci., (2006), vol. 68, pp. 295-300.
Aulton, M. E.—The science of dosage form design, (1988), pp. 316-321, (Churchill Livingstone Ed.), Pharmaceutics.
Banga, A. et al., "Incorporation of Simethicone into Syrup or Clear Base Liquid Orals", Drug Development and Industrial Pharmacy, (1989), vol. 15(5), pp. 671-704.
Conner, A. L. et al., A Scintigraphic Study to Investigate the Potential for Altered Gut Distribution of Loperaminde from a Loperaminde-Simethicone Formation in Man, European Journal of Pharmaceutical Sciences, (2001), vol. 13, pp. 369-374.
Dashevsky, A. et al., pH-independent Release of Baisc Drug from Pellets Coated with the Extended Release Polymer Dispersion Kollicoat® SR 30 D and the Enteric Polymer Dispersion Kollicoat® MAE 30 DP, European Journal of Pharmaceutics and Biopharmaceuticals, (2004), vol. 58, pp. 45-49 (available online Jun. 1, 2004).
Deshpande, A. et al., Development of a Novel Controlled-Release System for Gastric Retention, Pharmaceutical Research, (1997), vol. 14, No. 6, pp. 815-819.
Krögel, I. et al., Floating of Pulsatile Drug Delivery Systems Based on Coated Efferescent Cores, International Journal of Pharmaceutics, (1999) vol. 187, pp. 175-184 anl.
Laizure, S. C. et al., Stability of Bupropion and its Major Metabolites in Human Plasma, Therapeutic Drug Monitoring (1985), vol. 7 (4); p. 447.
Lehmann, K. et al.,—Fast Disintegrating Controlled Release Tablets from Coated Particles—Drugs Made in Germany, (1994) vol. 37, No. 2, pp. 53-60.
Martindale, The Extra Pharmacopoeia, 30th Ed. (The Pharmaceutical Press, London 1993).
Rakur, G. et al., 2-((2-Pyridylm-ethyl) Sulfiny) Benzimidazoles: Acid Sensitive Suicide Inhibitors of the Proton Transport System in the Parietal Cell, Biochem Biophys. Res. Comm. (1985), vol. 128, No. 1, pp. 477-484.
Remington's Pharmaceutical Sciences, 18th ed, (1990), Chapter 83, pp. 1539-1540.
Sathe, P.M. et al, Drug Product Performance, In Vitro, Generic Drug Product Development, (2004), vol. 143, Chapter 8, pp. 187-209.
Steward, P.A. Review of Pharmaceutical Controlled Release Method and Devices, (1995) 12 pages.
Sungthongjeen, S. et al.,—Development of Pulsatile Release Tablets with Swelling and Rupturable Layers, Journal of Controlled Release, (2004), vol. 95, pp. 1147-1159.
Sunshine, et al., "Analgesic Efficacy of Pentazocine Versus a Pentazocine-Naxloxone Combination Following Oral Administration", Clin. J. Pain, (1988), vol. 4, pp. 35-40.
Venkatraman et al., Chapter 22, An overview of Controlled Release Systems, Handbook of Pharmaceutical Controlled release Technology by Donald Wise, Published, (2002) p. 443.
Walters, S. M., Influence of pH on Hydrolytic Decomposition of Dimethylpropion Hydrochloride: Stability Studies on Drug Substance and Tables using High-Performance Liquid Chromatograph, J. Pharma Science, (1980), vol. 69 (10), p. 1208.
Wang, R. et al., Crossover and Parallel Study of Oral Analgesics, J. Clin. Pharmacl., (1981) Vo. 21, pp. 162-168.
Merriam-Webster Online Dictionary, http://www.meriam-webster.com/dictionary/prevent, obtained online Feb. 18, 2008.
Merriam-Webster Online Dictionary, http://www.meriam-webster.com/dictionary/cure, obtained online Dec. 16, 2009.
European Patent Application No. 04 737 76.2-2112, Examination Report dated Nov. 18, 2009.
Office Action for U.S. Appl. No. 10/561,700 dated Dec. 27, 2007.
Office Action for U.S. Appl. No. 10/561,700 dated Mar. 18, 2008.
Office Action for U.S. Appl. No. 10/561,700 dated Apr. 17, 2009.
Office Action for U.S. Appl. No. 10/561,700 dated Sep. 3, 2009.
Office Action for U.S. Appl. No. 10/861,809 dated Sep. 28, 2009.
Office Action for U.S. Appl. No. 10/861,809 dated Nov. 26, 2008.
Office Action for U.S. Appl. No. 10/861,809 dated Nov. 13, 2007.
Office Action for U.S. Appl. No. 12/092,654 dated Mar. 12, 2010.
Office Action for Canadian Patent Application No. 2,626,558 dated Nov. 25, 2009.
English translation of Office Action dated Oct. 13, 2010 corresponding to Chinese Patent Application No. 200780019372.7.
International Search Report and Written Opinion; PCT/CA2007/000540.
International Search Report and Written Opinion; PCT/CA2007/000548.
International Search Report and Written Opinion; PCTCA2007/000550.
International Search Report and Written Opinion; PCT/CA2007/000862.

International Search Report and Written Opinion mailed Aug. 31, 2007; PCT/CA2007/000862.
International Preliminary Report on Patentability mailed Nov. 27, 2008; PCT/CA2007/000862.
International Preliminary Examination Report; PCT/CA2002/01360.
International Search Report; PCT/CA2002/01360.
International Search Report; PCT/CA2002/00054.
International Search Report and Written Opinion; PCT/CA2004/000825.
Encyclopaedia of Polymer Science and Technology; vol. 10 (1969); published by John Wiley & Sons.
USPTO U.S. Appl. No. 11/473,386.
USPTO U.S. Appl. No. 09/947,464.
USPTO U.S. Appl. No. 10/561,700.
USPTO U.S. Appl. No. 12/696,118.
USPTO U.S. Appl. No. 12/225,956.
USPTO U.S. Appl. No. 12/225,954.
USPTO U.S. Appl. No. 11/432,226.
USPTO U.S. Appl. No. 12/092,654.
USPTO U.S. Appl. No. 10/924,649.
USPTO U.S. Appl. No. 10/900,415.
USPTO U.S. Appl. No. 10/880,474.
USPTO U.S. Appl. No. 11/315,868.
Torpac, Capsul Size Chart, 2000, pp. 1-3.
Paste, http://www.thefreedictionary.com/paste,accessed Jun. 29, 2012.
Supplemental European Search Report Prepared by Miralles J. Gimenez Aug. 23, 2012.
Supplemental European Search Report Prepared by Antonio Raposo Aug. 2, 2012.

* cited by examiner

CONTROLLED EXTENDED DRUG RELEASE TECHNOLOGY

BACKGROUND OF THE INVENTION

Efficacy and safety is paramount in the treatment of disease states with therapeutically active agents. Efficacy is usually as a result of the therapeutic agent reaching its target sites in amounts sufficient to maintain therapeutic levels for a desired period. It is now generally accepted that sustained release of a therapeutically active agent is desirable when treating chronic diseases conditions were current therapy dictates multiple daily dosing and were the half life of the therapeutic agent is short. With traditional sustained-release dosage formulations, particularly matrix based systems, when taken in the morning, the efficacy of the therapeutic agent diminishes at the end of the night and the beginning of the next day.

When therapeutics agents are administered orally they must enter the general circulation of the human body in order to reach their target sites of action. They are released in the GIT, and are absorbed into the capillaries and veins of the upper gastrointestinal tract, and transported by the portal vein to the liver. Following their absorption in the intestine, some orally administered therapeutic agents may be subject to a "first pass" clearance by the liver and excreted into bile or converted into pharmacologically inactive metabolites. This can result in a decrease in bioavailability due to the liver removing the therapeutic agent from the bloodstream prior to entering a patient's general circulation. For a therapeutic agent to overcome a first pass effect it has to be present in amounts that exceed the excretory or metabolic capability of the liver.

First pass metabolism makes it difficult to the maintain therapeutic levels of an orally administered therapeutic agent over an extended period such as 12 or 24 hours.

One way to overcome this problem is to administer formulations capable of immediate drug release multiple times daily (i.e., 2-4 times daily), but this approach may result in high peaks and low valley effects (i.e., toxic and sub-therapeutic levels) and compliance issues. Another way is to administer formulations, capable of sustained drug release, that are suitable for once-daily administration. Due to the need to reduce the difference between "peak and valley" concentrations and patient compliance issues, once-daily sustained release formulations are preferred. A sustained release formulation, however, may subject the patient to toxic drug levels over part of the dosing period, and sub-therapeutic drug levels over other portions of the dosing period, if the drug release does not occur at appropriate time intervals. The maintenance of therapeutic levels of an orally administered drug over an extended period thus depends upon a drug delivery system capable of providing an appropriate release profile.

It can be seen from the foregoing that there is a need in the art to develop a controlled extended drug release technology with or without a loading dose in a tablet, pellet or bead formulation suitable for a more precise zero, first or pseudo first order release of a therapeutic agent, and which, in situations where the drug is subject to "first pass" metabolism, can be used to provide sustained drug delivery, preferably over a 24-hour period, by an amount sufficient to exceed the liver's metabolic capacity and to maintain therapeutic levels.

It was unexpectedly discovered that controlled extended release technology can be used to improve the efficacy of therapeutic agents during the declining phase identified above.

BRIEF SUMMARY OF THE INVENTION

The present invention pertains to a controlled extended drug release technology suitable for oral administration. It was surprisingly discovered that the invention allows for precise control of the extended release profile of a drug-loaded tablet, pellet or bead. It was also surprisingly discovered that a tablet, pellet or bead containing a gas generator and surrounded by a coat made from a thermoplastic water insoluble cellulose ether or a mixture of the said thermoplastic polymer and acrylic polymers and superdisintegrant and optionally electrolyte, oil and antioxidant resulted in a hydrodynamically buoyant dosage form despite the density of the dosage form. The buoyancy allows for longer resident times in the stomach compared to conventional drug delivery systems.

Another surprising aspect is the discovery that the application of a final top coat made from cellulose esters and or acrylic polymers acts as a timing device which can be used to switch on the activity of the dosage form. This will be particularly useful for drugs that require chronotherapeutic delivery.

With respect to drugs subject to "first pass" metabolism and those with short half-life, controlled extended drug release can be achieved through the present invention via an optional electrolyte, oil and antioxidant in the coat, and a loading dose, this together with gas generator and thermoplastic coat provides a dose sufficient to exceed the liver's metabolic capacity and to maintain therapeutic levels, preferably throughout a 24-hour period.

Accordingly, an objective of the present invention is a tablet, pellet or bead that can provide a zero, first and pseudo first order release of therapeutic agent. A second objective of the present invention is a tablet, pellet and bead that is capable of controlled extended release of therapeutic agents over 24 hours. Another objective of the present invention is a single orally administrable tablet that can overcome the "first pass" effect by providing a controlled extended release dosage, with or without a loading dose, with drug release sufficient to exceed the liver's metabolic capacity, and then continue to maintain therapeutic drug levels, preferably over a 24-hour period. A further objective of the present invention is a tablet, pellet or bead which is hydrodynamically buoyant. Yet another objective of the present invention is a controlled extended drug release tablet, pellet or bead with a timing device which can be used to switch on the activity of the dosage form.

In a preferred embodiment of the invention, these and other objectives can be accomplished through a drug delivery system that exhibits controlled extended drug release.

In a preferred embodiment of the present invention, the tablet, pellet or bead consists of a homogeneous drug loaded central compartment containing a gas generator, optionally oil, and surrounded by a coat made from a thermoplastic water insoluble cellulose ether or a mixture of the said thermoplastic polymer and acrylic polymers and superdisintegrant and optionally electrolyte, oil and antioxidant. In another preferred embodiment of the invention, there is added a top coat made from cellulose esters and or acrylic polymers which acts as a timing device which can be used to switch on the activity of the dosage form. This is particularly useful for drugs that require chronotherapeutic delivery.

In yet another preferred embodiment, drugs subject to "first pass" metabolism and those with short half-life, controlled extended drug release can also be achieved via an optional electrolyte in the coat, and a loading dose. This together with gas generator and thermoplastic coat provides a dose sufficient to exceed the liver's metabolic capacity and to maintain therapeutic levels, preferably throughout a 24-hour period.

In a preferred embodiment of the present invention, the active agent in the central compartment can diffuse out, with aid of gas generated by the gas generator. If there is a loading dose present this will be released first. If electrolytes are present in the coat they will ionize and impact on the integrity of the coat. The superdisintegrants act as "spacers" within the coat in the presence of aqueous media, and also impact on the integrity of the coat. Aqueous media will penetrate through the thermoplastic water insoluble cellulose ether or a mixture of the said thermoplastic polymer and acrylic polymers coat into the central drug compartment and cause a cascade of events which include wetting and solution, emulsification, or suspension of the therapeutic agent(s) present and initiation of gas generation. The rate of input and extent of release of the therapeutic agent in the GIT and plasma, can be regulated by varying the composition and relative amounts of the oil and gas generators in the central drug compartment and also by varying the relative ratios of the thermoplastic water insoluble cellulose ether or a mixture of the said thermoplastic polymer and acrylic polymers and superdisintegrant and electrolytes and oil present in the coat(s). The rate of input and extent of release can also be modulated by the relative amount of loading dose, cellulose esters and acrylic polymer top coat used as a timing device if present.

The central drug compartment preferably comprises a combination of therapeutic agents or precursors or prodrugs and gas generators. The coating layer(s) are preferably comprised of thermoplastic water insoluble cellulose ethers or a mixture of the said thermoplastic polymers and superdisintegrants or a mixture of the said thermoplastic polymers and superdisintegrants and acrylic polymers or a mixture of the said thermoplastic polymers and superdisintegrants and acrylic polymers and electrolytes. The loading dose top coat preferably comprises of a loading dose of a therapeutic agent and or cellulose ethers and or acrylic polymers and or cellulose esters. The timing device top coat is preferably comprised of acrylic polymers and or cellulose esters. In these embodiments, once administered, the timing device or drug loading top coat if present dissolves away in the GIT, releases the loading dose and exposes the thermoplastic polymer coating layer(s) to GI fluids. The GI fluids cause the electrolytes to ionize and the superdisintegrants to swell and the acrylic polymers to form salts, thus impacting on the integrity of the coat walls or membrane or film, allowing GI fluids to penetrate into the central drug compartment, wetting and dissolving the drug and triggering the formation of gases. Drug is released by migration and diffusion through the thermoplastic polymer coat. The central drug compartment preferably comprises a compressed, extruded or layered blend of active agent and gas generators and optionally oil, which upon exposure to the GI fluid, forms an emulsion, suspension, solution and gas to provide preferably complete drug release.

In another embodiment, the loading dose top coat and or timing device top coat can be modified so there are multiple peaks in drug concentration during in-vitro or in-vivo drug release. In yet another preferred embodiment the loading dose top coat and or timing device top coat can be modified so if orally administered before bedtime, this controlled extended drug delivery system could deliver its active agent while the patient is asleep to facilitate optimal therapeutic drug levels just prior to awakening. This is also suitable for drugs that require chronotherapeutic delivery or ailments that mimic the body's circadian rhythm.

Other objects, features and advantages of the present invention will become apparent from the following detailed description. The detailed description and the specific examples, however, indicate only preferred embodiments of the invention.

Various changes and modifications within the spirit and scope of the invention will become apparent to those skilled in the art from this detailed description.

DETAILED DESCRIPTION OF THE INVENTION

In a preferred embodiment, the water insoluble thermoplastic polymer is either cellulose or neutral ester copolymer (e.g., neutral methacrylic acid esters such as Eudragit® NE, Eudragite® RL, and Eudragit® RS) or mixture thereof.

In still another preferred embodiment, the loading dose is provided by the same or different therapeutic agent(s) in the central drug compartment.

In yet another preferred embodiment there is present one or more surface active agents and as an example glyceryl monooleate, sodium lauryl sulphate or glyceryl monostearate.

In a preferred embodiment, release of therapeutic agent is characterized by a dissolution profile in which at least 0.5% to 50% of the therapeutic agent is released within two hours, and greater than 50% is released in 24 hours, or by a dissolution profile in which at least 0.5% to 50% of the therapeutic agent is released within three hours, and greater than 50% is released in 24 hours, or by a dissolution profile in which at least 0.5% to 50% of the therapeutic agent is released within fours hours, and greater than 50% is released in 24 hours, or by a dissolution profile in which at least 0.5% to 50% of the therapeutic agent is released within five hours, and greater than 50% is released in 24 hours, or by a dissolution profile in which at least 0.5% to 50% of the therapeutic agent is released within six hours, and greater than 50% is released in 24 hours, or by a dissolution profile in which at least 0.5% to 50% of the therapeutic agent is released within eight hours, and greater than 50% is released in 24 hours, or by a dissolution profile in which at least 0.5% to 50% of the therapeutic agent is released within twelve hours, and greater than 50% is released in 24 hours, or by a dissolution profile in which at least 0.5% to 50% of the therapeutic agent is released within sixteen hours, and greater than 50% is released in 24 hours The oils used in the invention can be one or more selected from Almond Oil, Apricot Kernel Oil, Avocado Oil, Black Currant Oil, 14% GLA, Borage Oil, 20% GLA, Canola Oil, Carrot Oil, Castor Oil, Clove Leaf Oil, Coconut Oil, Corn Oil, Cottonseed Oil, Evening Primrose Oil, 9% GLA, Flaxseed Oil, 55% ALA, Grapeseed Oil, Hazelnut Oil, Hemp Oil, ALA / GLA, Hydrogenated Oils, Jojoba Oil, Golden Jojoba Oil, Water-white Kukui Nut Oil, Macadamia Nut Oil, Oat Oil, Olive Oil, Extra Virgin Olive Oil Pomace/"B" grade, Olive Oil, Pure/NF, Palm Oil, Parsley Seed Oil, Peach Kernel Oil, Peanut Oil, Pecan Oil, Pistachio Oil, Pumpkinseed Oil, Rice Bran Oil, Rose Hip Seed Oil, Rosemary Oil, Safflower Oil, Linoleic' Safflower Oil, High-Oleic, Sesame Oil NF, Sesame Oil Toasted, Soybean Oil, Sunflower Oil, Salad Sunflower Oil High-Oleic, Tea Tree Oil, Vegetable, Glycerine, USP, Walnut Oil, Wheat Germ Oil, Cold-pressed and mineral oil or other similar oils.

The gas generators used in the invention can be selected from soluble or insoluble acid sources such as food acids (citric acid, tartaric acid, lactic acid, malic acid, fumaric acid, ascorbic acid, adipic acid, succinic acid); acid anhydrides (succinic anhydride, citric anhydride); acid salts (sodium dihydrogen phosphate, disodium dihydrogen pyrophosphate, sodium dihydrogen citrate, disodium hydrogen citrate) and carbonate sources (sodium bicarbonate, sodium carbonate, potassium bicarbonate, potassium carbonate, sodium sesquicarbonate, sodium glycine carbonate, lysine carbonate, arginine carbonate, amorphous calcium carbonate); and oxygen gas generators such as anhydrous sodium perborate or other suitable generators The antioxidants used in this invention may be selected from ascorbic acid, fumaric acid, malic acid, alpha tocopherol, ascorbic acid palmitate, butylated hydroxyanisole, propyl gallate, sodium ascobate, and sodium metabisulfite or other suitable antioxidants The said invention also accomplishes these and other objectives through a method for preparing a tablet, pellet or bead for use in controlled extended release of therapeutic agent in which dry or wet granulation of an effective amount of therapeutic active agent, or a pharmaceutically acceptable salt thereof, and dry or wet granulating aids, tableting aids and gas generators and optionally oil is carried out using high shear or low shear mixers or fluidbed granulators. If required, the granules are dried, sieved, lubricated, blended before being compressed to form a tablet or pellet to form a central compartment. This is followed by coating using fluid bed or pan coating techniques to apply one or more coats of thermoplastic cellulose ether in combination with an acrylic polymer and or cellulose esters and superdisintegrant and optionally oil and electrolytes. Additionally, a top coat may be added for the purpose of delivering a loading dose and or serving as a timing device made from acrylic polymers or cellulose esters.

A preferred embodiment further includes the steps of combining an effective amount of a therapeutic active agent, or a pharmaceutically acceptable salt thereof, gas generators, optionally oil, and extrusion spheronization aids to form beads or pellets made from extrusion spheronization techniques. The beads may also be made by drug powder or solution layering. The beads formed are coated using fluid bed or pan coating to apply one or more coats of thermoplastic cellulose ether in combination with an acrylic polymer and or cellulose esters and superdisintegrant and optionally oil and electrolytes and antioxidants. Additionally a top coat may be added for the purpose of serving as a loading dose and or serving as a timing device made from acrylic polymers or cellulose esters.

In a preferred embodiment, a pharmaceutically acceptable acrylic polymer, includes, but is not limited to, acrylic acid and methacrylic acid copolymers, methyl methacrylate copolymers, ethoxyethyl methacrylates, cyanoethyl methacrylate, aminoalkyl methacrylate copolymer, poly(acrylic acid), poly(methacrylic acid), methacrylic acid alkylamide copolyer, poly(methyl methacrylate), poly(methyl methacrylate) copolymer, polyacrylamide, aminoalkyl methacrylate copolymer, poly(methacrylic acid anhydride), and glycidyl methacrylate copolymers. Additionally, the acrylic polymers may be cationic, anionic, or non-ionic polymers and may be acrylates, methacrylates, formed of methacrylic acid or methacrylic acid esters. The polymers may also be pH independent or pH dependent.

It is to be understood that more than one therapeutically active agent may be incorporated into the device of this invention, and that the use of the term "agent" or "drug" in no way excludes the use of two or more such agents or drugs. The therapeutic agents can be in various forms, such as uncharged molecules, components of molecular complexes or nonirritating, pharmacologically acceptable salts. Also, simple derivatives of the agents (such as ethers, esters, amides, etc.) which are easily hydrolyzed by body pH, enzymes, etc., can be employed.

The term "therapeutically active agent", or "therapeutic agent", or "active agent" as used herein refers to an agent, drug, compound, composition of matter or mixture thereof which provides some biological, often beneficial, effect. This includes pesticides, herbicides, germicides, biocides, algaecides, rodenticides, fungicides, insecticides, antioxidants, plant growth promoters, plant growth inhibitors, preservatives, antipreservatives, disinfectants, sterilization agents, catalysts, chemical reactants, fermentation agents, foods, food supplements, nutrients, cosmetics, drugs, vitamins, sex sterilants, fertility inhibitors, fertility promoters, microorganism attenuators and other agents that benefit the environment of use. As used herein, the terms further include any physiologically or pharmacologically active substance that produces a localized or systemic effect or effects in animals, including warm blooded mammals, humans and primates; avians; domestic household or farm animals such as cats, dogs, sheep, goats, cattle, horses and pigs; laboratory animals such as mice, rats and guinea pigs; fish; reptiles; zoo and wild animals; and the like.

The active agent that can be delivered includes inorganic and organic compounds, including, without limitation, drugs which act on the peripheral nerves, adrenergic receptors, cholinergic receptors, the skeletal muscles, the cardiovascular system, smooth muscles, the blood circulatory system, synoptic sites, neuroeffector junctional sites, endocrine and hormone systems, the immunological system, the reproductive system, the skeletal system, autacoid systems, the alimentary and excretory systems, the histamine system and the central nervous system. Suitable active agents may be selected from, for example, proteins, enzymes, hormones, polynucleotides, nucleoproteins, polysaccharides, glycoproteins, lipoproteins, polypeptides, steroids, hypnotics and sedatives, psychic energizers, tranquilizers, anticonvulsants, muscle relaxants, antiparkinson agents, analgesics, anti-inflammatories, local anesthetics, muscle contractants, antimicrobials, antimalarials, hormonal agents including contraceptives, sympathomimetics, polypeptides and proteins capable of eliciting physiological effects, diuretics, lipid regulating agents, antiandrogenic agents, antiparasitics, neoplastics, antineoplastics, hypoglycemics, nutritional agents and supplements, growth supplements, fats, ophthalmics, antienteritis agents, electrolytes and diagnostic agents.

Examples of beneficial active agents useful in this invention include prochlorperazine edisylate, ferrous sulfate, aminocaproic acid, mecaxylamine hydrochloride, procainamide hydrochloride, amphetamine sulfate, methamphetamine hydrochloride, benzphetamine hydrochloride, isoproteronol sulfate, phenmetrazine hydrochloride, bethanechol chloride, methacholine chloride, pilocarpine hydrochloride, atropine sulfate, scopolamine bromide, isopropamide iodide, tridihexethyl chloride, phenformin hydrochloride, methylphenidate hydrochloride, theophylline cholinate, cephalexin hydrochloride, diphenidol, meclizine hydrochloride, prochlorperazine maleate, phenoxybenzamine, thiethylperazine maleate, anisindione, diphenadione erythrityl tetranitrate, digoxin, isoflurophate, acetazolamide, methazolamide, bendroflumethiazide, chlorpropamide, tolazamide, chlormadinone acetate, phenaglycodol, allopurinol, aluminum aspirin, methotrexate, acetyl sulfisoxazole, hydrocortisone, hydrocorticosterone acetate, cortisone acetate, dexamethasone and its derivatives such as betamethasone, triamcinolone, methyltestosterone, 17-.beta.-estradiol, ethinyl estradiol, ethinyl estradiol 3-methyl ether, prednisolone, 17-.beta.-hydroxyprogesterone acetate, 19-nor-progesterone, norgestrel, norethindrone, norethisterone, norethiederone, progesterone, norgesterone, norethynodrel, aspirin, indomethacin, naproxen, fenoprofen, sulindac, indoprofen, nitroglycerin, isosorbide dinitrate, propranolol, timolol, atenolol, alprenolol, cimetidine, clonidine, imipramine, levodopa, chlorpromazine, methyidopa, dihydroxyphenylalanine, theophylline, calcium gluconate, ketoprofen, ibuprofen, cephalexin, erythromycin, haloperidol, zomepirac, ferrous lactate, vincamine, phenoxybenzamine, milrinone, captropril, mandol, quanbenz, hydrochlorothiazide, ranitidine, flurbiprofen, fenbufen, fluprofen, tolmetin, alclofenac, mefenamic, flufenamic, difuninal, nimodipine, nitrendipine, nisoldipine, nicardipine, felodipine, lidoflazine, tiapamil, gallopamil, amlodipine, mioflazine, lisinopril, enalapril, captoril, ramipril, enalaprilat, famotidine, nizatidine, sucralfate, etintidine, tetratolol, minoxidil, chlordiazepoxide, diazepam, amitriptylin, and imipramine. Further examples are proteins and peptides which include, but are not limited to, insulin, colchicine, glucagon, thyroid stimulating hormone, parathyroid and pituitary hormones, calcitonin, renin, prolactin, corticotrophin, thyrotropic hormone, follicle stimulating hormone, chronic gonadotropin, gonadotropin releasing hormone, bovine somatotropin, porcine somatropin, oxytocin, vasopressin, prolactin, somatostatin, lypressin, pancreozymin, luteinizing hormone, LHRH, interferons, interleukins, growth hormones such as human growth hormone, bovine growth hormone and porcine growth hormone, fertility inhibitors such as the prostaglandins, fertility promoters, growth factors, and human pancreas hormone releasing factor.

As used herein, the terms "therapeutically effective" amount or rate refer to the amount or rate of the active agent needed to achieve the desired therapeutic result.

The following examples are illustrative only, and not limiting of the remainder of the disclosure in any way whatsoever.

EXAMPLE 1

(I) Formula of Drug Containing Central Compartment

|  | Formulation1 (%) | Formulation2 (%) | Formulation3 (%) | Formulation4 (%) | Formulation5 (%) |
|---|---|---|---|---|---|
| Carvedilol | 10 | 10 | 10 | 10 | 10 |
| Microcrystalline cellulose | 25 | 25 | 25 | 72 | 70 |
| Lactose | 47.26 | 56 | 37.7 | — | — |
| Silicone dioxide | 1 | 1 | 1 | 1 | — |
| Tartaric acid | — | — | 2 | — | — |
| Citric acid | 3.51 | 10 | 4 | 5 | 5 |
| Calcium carbonate | 1.23 | — | — | — | — |
| Sodium bicarbonate | — | 12 | 6.8 | 6 | 6 |
| Mineral oil | — | 2.5 | — | — | — |
| Coconut oil | 2.5 | — | 3 | 1 | 1 |
| Glyceryl monooleate | — | 2 | 3 | — | 1 |
| Sodium lauryl sulphate | — | 3 | — | — | 7 |
| Polysorbate 80 | 10 | 5 | 7 | 5 | — |
| Magnesium Stearate | 0.5 | 0.5 | 0.5 | — | — |
| Total | 100 | 100 | 100 | 100 | 100 |

(II) Manufacture of Drug Containing Tablets/Pellets

Formulation 1, 2 or 3 may be used to make tablets or pellets. Carvedilol is mixed with microcrystalline cellulose, tartaric acid and or citric acid, calcium carbonate or sodium bicarbonate, oil, glyceryl monooleate, sodium lauryl sulphate, polysorbate 80 and silicon dioxide in a high-shear or low shear mixer granulator or Patterson-Kelley V-blender for 10 minutes. The mixture is then granulated with an organic solvent and dried. Granulation may be done in a fluidbed. Magnesium stearate is added to the dried granules and blended for 5 more minutes in a V-blender. The powder blend is then compressed using an Elizabeth Hata rotary tablet press.

(III) Manufacture of Drug Loaded Beads/Pellets

Formulation 4 or 5 may be used to make beads. Carvedilol, microcrystalline cellulose, citric acid, sodium bicarbonate, Sodium lauryl sulphate, polysorbate 80, glyceryl monooleate and oil are dry mixed in a low shear mixer and wet granulated. The wet mass is extruded and spheronized using a Caleva extruder and spheronizer. The spheronized beads are dried.

(IV) Coating of Tablets, Pellets or Beads

Ethylcellulose is dissolved in alcoholic solution. To this is added an acrylic polymer (Eugragit L and Eudragit S), super disintegrant (Crospovidone) and oil (Coconut oil). This is sprayed on the tablets (using a side vented pan coater), pellets or beads (using a fluid bed coater) to form a coat or coats around them to a weight gain of from about 1.0% to about 25%.

EXAMPLE 2

(I) Formula of Drug Containing Central Compartment

|  | Formulation1 (%) | Formulation2 (%) | Formulation3 (%) | Formulation4 (%) | Formulation5 (%) |
|---|---|---|---|---|---|
| Venlafaxine Hcl | 10 | 10 | 10 | 10 | 10 |
| Microcrystalline cellulose | 25 | 25 | 25 | 75 | 78 |
| Lactose | 47.26 | 64 | 47.7 | — | — |
| Silicone dioxide | 1 | 1 | 1 | 1 | — |
| Tartaric acid | — | — | 2 | — | — |
| Citric acid | 10.51 | 10 | 4 | 5 | 5 |
| Calcium carbonate | 4.23 | — | — | — | — |
| Sodium bicarbonate | — | 12 | 6.8 | 6 | 6 |
| Mineral oil | — | 2.5 | — | — | — |
| Coconut oil | 2.5 | — | 3 | 1 | 1 |
| Polysorbate 80 | — | 2 | — | 2 | — |
| Magnesium Stearate | 0.5 | 0.5 | 0.5 | — | — |
| Total | 100 | 100 | 100 | 100 | 100 |

(II) Manufacture of drug containing tablets/Pellets

Formulation 1, 2 or 3 may be used to make tablets or pellets. Venlafaxine is mixed with microcystalline cellulose, tartaric acid and or citric acid, calcium carbonate or sodium bicarbonate, oil, polysorbate 80 and silicon dioxide in a high-shear or low shear mixer granulator or Pafterson-Kelley V-blender for 10 minutes. The mixture is then granulated with an organic solvent and dried. Granulation may be done in a fluidbed. Magnesium stearate is added to the dried granules and blended for 5 more minutes in a V-blender. The powder blend is then compressed using an Elizabeth Hata rotary tablet press.

(III) Manufacture of Drug Loaded Beads/Pellets

Formulation 4 or 5 may be used to make beads. Venlafaxine, microcrystalline cellulose, citric acid, sodium bicarbonate, polysorbate 80, and oil are dry mixed in a low shear mixer and wet granulated. The wet mass is extruded and spheronized using a Caleva extruder and spheronizer. The spheronized beads are dried.

(IV) Coating of Tablets, Pellets or Beads

Ethylcellulose is dissolved in alcoholic solution. To this is added Hydroxypropylmethyl cellulose acetate, super disintegrant and sodium chloride. This is sprayed on the tablets, pellets or beads to form a coat or coats around them to a weight gain of from about 1.0% to about 25%.

(V) Composition and Addition of Loading Dose of Venlafaxine 5% wt by wt.

A loading dose consisting of Venlafaxine is applied as a coat to a weight gain of about 5%. This consists of venlafaxine in a hydroxypropylmethyl cellulose binder solution.

(VI) Composition and Addition of Top Coat.

The coat is made from Eudragit L and S in ratio of 5:1. and is applied to a coating thickness of from about 1% to about 50% weight gain

EXAMPLE 3

This is the same as example 2 except that venlafaxine is replaced by paroxetine hydrochloride and sodium chloride is added to the ethylcellulose coat.

EXAMPLE 4

This is the same as example 2 except that venlafaxine is replaced by metoprolol succinate and sodium chloride and coconut oil are added to ethylcellulose coat

EXAMPLE 5

This is the same as example 2 except that venlafaxine is replaced by metoprolol succinate and ascorbic acid, sodium chloride and coconut oil are added to the cellulose coat.

We claim:

1. A formulation, comprising:
   (a) a central compartment containing a homogeneous blend of one or more therapeutic agents, a gas generator and optionally oils, antioxidants and surface active agents;
   (b) one or more tableting, extrusion and coating aids;
   (c) one or more layers of coat surrounding the central compartment, the coat comprising one or more thermoplastic water insoluble cellulose ethers and esters and one or more acrylic polymers; and
   (d) wherein release of therapeutic agent from said formulation is characterized by a dissolution profile in which 0.5% to 50% of the therapeutic agent is released within three hours, and greater than 50% is released in 24 hours; and
   wherein the formulation is a hydrodynamically buoyant dosage form.

2. The formulation according to claim 1 wherein the cellulose ethers and esters is ethyl cellulose.

3. The formulation according to claim 1 wherein the coat further comprises one or more superdisintegrants.

4. The formulation according to claim 1 wherein the coat further comprises one or more electrolytes.

5. The formulation according to claim 4 wherein the gas generator consist of a soluble or insoluble acid source and an alkali metal carbonate.

6. The formulation according to claim 1 wherein the acrylic polymer is selected from one or a mixture of anionic polymers based on methacrylic acid esters, methacrylates copolymer and or copolymers of acrylate and methacrylates and or ethylacrylate methylmethacrylate copolymers.

7. The formulation according to claim 3 wherein the superdisintegrant is selected from one or a mixture of croscarmelose, sodium starch glycolate, and crospovidone.

8. The formulation according to claim 4 wherein the cellulose ethers and esters is ethylcellulose.

9. The formulation according to claim 4 wherein the electrolyte is chosen from one or a mixture of salts capable of providing, sodium ($Na^+$), potassium ($K^+$), chloride ($Cl^-$), calcium (Ca$^{2+}$), magnesium (Mg$^{2+}$), bicarbonate (HCO$_3^-$), phosphate (PO$_4^{2-}$), sulfate (SO$_4^{2-}$) ions.

10. The formulation according to claim 1 wherein the coat contains one or more oils.

11. The formulation according to claim 1 wherein the coat includes shellac and or Zein.

12. The formulation according to claim 10 wherein the oil is chosen from one or a mixture of animal, plant or synthetic origin.

13. The formulation according to claim 1 wherein the acrylic polymer, is chosen from one or a mixture of, methyl methacrylate copolymers, ethoxyethyl methacrylates, cyanoethyl methacrylate, aminoalkyl methacrylate copolymer, poly(acrylic acid), poly(methacrylic acid), methacrylic acid alkylamide copolyer, poly(methyl methacrylate), poly(methyl methacrylate) copolymer, polyacrylamide, aminoalkyl methacrylate copolymer, poly(methacrylic acid anhydride), and glycidyl methacrylate copolymers.

14. The formulation according to claim 1 wherein one of said one or more layers is a final top coat that is made from cellulose esters or acrylic polymers or a mixture thereof.

15. The formulation according to claim 14 wherein one of said one or more layers is a final top coat that contains a loading dose.

16. The formulation according to claim 1 wherein there is present a surface active agent.

17. The formulation according to claim 1 wherein the gas generator is an oxygen generator.

18. The formulation according to any one of claims 1 to 5, wherein the formulation is in a form selected from a tablet, a pellet, or a bead.

19. A formulation, comprising:
  (a) a central compartment containing a homogeneous blend of one or more therapeutic agents, a gas generator and optionally oils, antioxidants and surface active agents;
  (b) a coat surrounding the central compartment, comprising one or more thermoplastic water insoluble cellulose ethers and esters and one or more acrylic polymers and a superdisintegrant; and
  (c) a loading dose top coat comprising a loading dose of a therapeutic agent;
  wherein release of therapeutic agent from said formulation is characterized by a dissolution profile in which 0.5% to 50% of the therapeutic agent is released within three hours, and greater than 50% is released in 24 hours; and
  wherein the formulation is a hydrodynamically buoyant dosage form.

* * * * *